United States Patent [19]
Zimmermann et al.

[11] Patent Number: 5,424,037
[45] Date of Patent: Jun. 13, 1995

[54] APPARATUS FOR HANDLING LIQUID VIALS IN AN ANALYTICAL DEVICE

[75] Inventors: Hans-Peter Zimmermann, Karlsbad; Fred Strohmeier, Rheinmuenster; Klaus Witt, Keltern, all of Germany

[73] Assignee: Hewlett-Packard Company, Palo Alto, Calif.

[21] Appl. No.: 261,026

[22] Filed: Jun. 15, 1994

Related U.S. Application Data

[63] Continuation of Ser. No. 86,589, Jul. 1, 1993, abandoned.

[30] Foreign Application Priority Data

Aug. 4, 1992 [EP] European Pat. Off. ........... 92113245

[51] Int. Cl.[6] .................... G01N 27/26; G01N 27/447
[52] U.S. Cl. .................................. 422/64; 204/299 R
[58] Field of Search ........................ 422/63, 64, 70, 99, 422/100; 436/47, 48, 149, 150, 161, 806, 43; 204/299 R, 301

[56] References Cited

U.S. PATENT DOCUMENTS

| | | | |
|---|---|---|---|
| 4,476,733 | 10/1984 | Chlosta et al. | 422/64 X |
| 4,478,095 | 10/1984 | Bradley et al. | 422/64 X |
| 4,506,777 | 3/1985 | Kampf | 198/341 |
| 4,705,667 | 11/1987 | Marsoner et al. | 422/68.1 |
| 4,713,974 | 12/1987 | Stone | 422/64 X |
| 4,927,265 | 5/1990 | Brownlee et al. | 356/73 |
| 4,951,512 | 8/1990 | Mazza et al. | 422/64 X |
| 5,009,760 | 4/1991 | Zare et al. | 204/299 R X |
| 5,032,361 | 7/1991 | Kleinhappl et al. | 422/67 |
| 5,089,230 | 2/1992 | Kondo et al. | 422/64 |
| 5,131,997 | 7/1992 | Christianson et al. | 204/229 R |
| 5,169,511 | 12/1992 | Allington et al. | 204/299 R |
| 5,171,531 | 12/1992 | Christianson et al. | 422/67 X |
| 5,173,163 | 12/1992 | Tehrani | 204/299 R |
| 5,232,665 | 8/1993 | Burkovich et al. | 422/65 |
| 5,240,576 | 8/1993 | Lauer et al. | 204/299 R X |
| 5,301,261 | 4/1994 | Poole et al. | 422/64 X |

FOREIGN PATENT DOCUMENTS

| | | |
|---|---|---|
| 0339779 | 11/1989 | European Pat. Off. |
| 0383459A2 | 8/1990 | European Pat. Off. |
| 0475533A2 | 3/1992 | European Pat. Off. |
| 4105059 | 4/1992 | Japan |

OTHER PUBLICATIONS

"Characterization and Automation of Sample Introduction Methods for Capillary Zone Electrophoresis", D. J. Rose et al, Apr. 1988, vol. 60, No. 7, pp. 642-648 Analytical Chemistry.

*Primary Examiner*—Robert J. Warden
*Assistant Examiner*—Robert Carpenter

[57] ABSTRACT

An apparatus for handling liquid vials in an analytical device comprises a single movable tray for accommodating a plurality of vials, and lifting devices arranged in the proximity of the tray for lifting vials out of the tray. The tray has a plurality of recesses for holding the vial. The recesses are open at the bottom so that a vertically movable finger of a lifting device which can be positioned underneath the bottom of a vial can move the vial out of the tray by an upward movement. When a vial has been lifted out of the tray, the tray remains freely rotatable so that a different vial can be positioned at a further lifting device and then lifted out of the tray. The invention provides a mechanically simple apparatus which is particularly suited for capillary electrophoresis for handling vials containing sample and electrolyte liquid. In capillary electrophoresis, two of the lifting devices are used for lifting vials to the ends of an electrophoresis capillary and a further lifting device is used for moving electrolyte vials to an arrangement for replenishing the electrolyte.

12 Claims, 3 Drawing Sheets

APPARATUS FOR HANDLING LIQUID VIALS IN AN ANALYTICAL DEVICE

This is a continuation of application Ser. No. 08/086,589 filed on Jul. 1, 1993, now abandoned.

The invention relates to an apparatus for handling liquid vials in an analytical device, in particular in a device for performing capillary electrophoresis.

BACKGROUND OF THE INVENTION

Capillary electrophoresis is a separation method employed in analytical chemistry which utilizes the differences in electrophoretic mobility of the sample substances to be separated. Capillary electrophoresis is used, for example, for separating different biological molecules, such as proteins or peptides. The separation process is performed in a capillary tube which is open on both ends and to which an electric field is applied which causes electrophoretic separation of different sample substances within the tube. The electric field is applied by means of electrodes which are arranged at the ends of the capillary, respectively, and which are connected to a high voltage power supply. The capillary is filled with an electrically conductive electrolyte so that an electric field can build up within the capillary. The two ends of the capillary are immersed in vials containing the electrolyte, respectively.

When new sample substances are to be introduced into the capillary for subsequent separation, the vial containing the electrolyte is removed from one end of the capillary, a vial containing the sample is positioned at this place so that the end of the capillary is immersed in the sample liquid. Thereafter, the sample is injected into the capillary by a suitable method, for example by applying a pressure above atmospheric pressure at the end of the capillary where the vial is positioned or a vacuum at the other end of the capillary. When the sample substances have been injected into the capillary, the sample vial is removed and the electrolyte vial is again positioned at this place. Thereafter, high voltage is applied so that electrophoretic separation of the sample substances takes place. At the end of the capillary opposite to the end of sample injection, a detector is arranged for detecting the separated sample substances by a suitable detection method, for example by a light absorption or a fluorescence technique.

After several electrophoretic separations have been performed, it may be necessary to draw off electrolyte from the electrolyte vial to avoid accumulation of products generated by electrochemical processes due to the current flowing in the capillary. If electrolyte has been drawn off or is otherwise missing in the electrophoretic system, it has to be replenished.

From the above, it becomes apparent that for performing capillary electrophoresis, a plurality of manipulations involving liquids have to be performed, such as immersing the two ends of the capillary in electrolyte, conveying sample liquid to an end of the capillary, replenishing the electrolyte. As these liquids are typically stored in vials, it is necessary to perform a plurality of movements of the vials and/or the separation capillary. In order to provide an electrophoresis device which is capable of automatically performing chemical analyses, an apparatus for handling liquid vials is required which performs the mentioned mechanical movements of vials and/or the capillary.

In the prior art, several different concepts for handling liquid vials in capillary electrophoresis are known. According to a first approach, a stationary electrolyte reservoir which cannot be changed is arranged at the outlet end of the capillary. The inlet end of the capillary is moved by a corresponding mechanism to the sample and electrolyte vials. This approach has several disadvantages: Since the ends of the capillary are not at the same level during the separation process, a hydrodynamic pressure difference is created between the ends of the capillary, whereby the separation efficiency is reduced. Furthermore, liquids for the preparation and for carrying out the electrophoretic separation can only be changed at the inlet end of the capillary. This limits the versatility of the apparatus. An additional disadvantage is that separated sample fractions cannot be collected at the outlet end of the capillary.

According to a second known solution for handling liquid vials, a stationary electrolyte reservoir is arranged at the outlet end of the capillary and a circular magazine containing sample and electrolyte vials is arranged at the inlet end of the capillary. A lifting mechanism is provided to lift sample and electrolyte vials such that the capillary end is immersed in the corresponding liquid. The disadvantages of this apparatus are like in the previously mentioned prior an apparatus that liquids for the preparation and for carrying out the electrophoretic separation can only be changed at the inlet end of the capillary. Furthermore, separated sample fractions cannot be collected at the outlet end of the capillary.

In another vial handling apparatus of the prior art, both ends of the capillary are fixed. Near both ends of the capillary, a circular magazine containing sample and electrolyte vials is provided. These two magazines may be operated independently of each other. The sample and electrolyte vials may be lifted so that the capillary ends dip into the corresponding liquid. A liquid handling apparatus of this type is known from EP-A-0 339 779. This known apparatus comprises two concentric conveyors which can be rotated around a common axis. The conveyors comprise septum sealed vials which can be conveyed into registry underneath a cartridge containing a capillary for capillary electrophoresis. The vials, each held in a vial holder are conveyed until one vial on one conveyor underlies one depending capillary end and the other vial on the other conveyor underlies the other depending capillary end. When registry of the vials to the capillary ends has been made, the vials are moved upwardly by piston-assisted movement of vial holders with respect to the-conveyors until the vials are pierced at a sealing septum by hypodermics. After piercing by the hypodermics, the piston-assisted movement continues to thread the hypodermic with either a capillary or an electrode for access to the content of the interior of the vial.

The known apparatus has the disadvantage that it is mechanically very complex since it requires two magazines for the vials, each with a driving motor and a lifting mechanism. Furthermore, there is a fixed correspondence of the vials to a certain end of the capillary, i.e., the vials which can be positioned at the inlet end of the capillary cannot be positioned at the outlet end of the capillary and vice versa.

SUMMARY OF THE INVENTION

It is thus an object of the present invention to provide an apparatus for handling liquid vials in an analytical device, in particular in a capillary electrophoresis device, which has a simpler construction than the prior art apparatuses.

It is a further object of the invention to provide an apparatus for handling liquid vials in an analytical device which is more-versatile than prior art apparatuses and does not have the mentioned further limitations of the known apparatuses.

According to the present invention, these objects are solved by an apparatus as defined in the claims. The apparatus of the invention comprises a single movable tray for receiving the vials, for example vials containing sample or electrolyte liquid, with the tray comprising a plurality of vial holders for holding the vials, respectively; the apparatus further comprises at least one lifting device arranged in the proximity of the tray for lifting a vial out of its vial holder, and drive means for moving the tray such as to position a selectable vial in the proximity of the lifting device. It is an underlying principle of the invention that the vials used in the operation of the analytical device are arranged in a single, movable tray and that these vials ban be lifted out of the tray and positioned at desired locations in the analytical device, for example at an end of an electrophoresis capillary, by a lifting device such that the tray remains movable when the vial has been lifted out of the tray. Since the tray remains movable after lifting a vial out of the tray, several operations involving different vials can be performed in parallel. If several lifting devices are provided in the proximity of the tray, a first vial can be lifted by a first lifting device to perform any manipulations with the liquid in the vial, then the tray can be moved so that a second lifting device can lift a second vial out of the tray, etc. Thus, it is possible to perform manipulations with the liquids in several vials in parallel.

In contrast thereto, the above mentioned prior art vial handling device does not permit such parallel operations since the tray is blocked if a vial has been lifted out of the tray. Since the apparatus of the invention has only a single tray, it is mechanically less complex than the prior art apparatuses; in particular, only one drive means for the movement of the tray is required. Furthermore, the use of only one tray ensures a great versatility of the apparatus. Each vial may be positioned at any place in the tray, whereas in the prior art apparatuses which comprise several trays (magazines), the user has to decide in advance which vial to put in which tray since the vials in the different trays are transported to different locations in the analytical device.

In a preferred embodiment of the invention, the vial handling apparatus is used in a device for performing capillary electrophoresis. According to this embodiment, at least two lifting devices are arranged in the proximity of the tray, one lifting device for each end of the capillary. The capillary ends depend vertically downwards and the vials are lifted towards the capillary ends Until they are immersed in electrolyte or sample liquid. It is a particular advantage of the invention that after lifting vials to the ends of the capillary, respectively, the tray may be turned in order to position a third vial at another lifting device where liquid manipulations can be performed. This third lifting device may comprise means for sucking off and replacing liquid such as electrolyte. Thus, electrolyte can be replenished while an electrophoretic separation takes place. Furthermore, the invention allows to replenish electrolyte while the separation column is rinsed.

Since the lifting devices in an embodiment of the invention can be moved up and down by a desired distance, it is possible to adjust the relative liquid levels of the liquids contained in the vials. This is particularly important in capillary electrophoresis wherein hydrostatic pressure differences between the vials at the end of the capillary would lead to liquid movements in the capillary. The lifting devices in the invention can be adjusted such that the levels are equal during electrophoresis. Also, a level difference could be adjusted between the two vials to effect a sample injection due to hydrostatic pressure differences.

An additional advantage of the invention when used in connection with an electrophoresis device is that the replenishment system can be arranged spatially separated from the high voltage electrodes. Thus, no further protective measures are required to protect the replenishment system of high voltage spark-over.

A further advantage of the invention in an electrophoresis device is that sample fractions can be collected at the outlet end of the capillary since the outlet end of the capillary is accessible. The apparatus of the invention can easily be expanded by adding further lifting devices, for example for performing sample preparation. Such additional lifting devices may comprise means for heating or mixing sample liquids.

In an embodiment of the invention, the lifting device comprises a finger-like lifting element which can be positioned underneath a vial and which can be lifted to move the vial upwards out of the tray. The tray has a plurality of bores for receiving the vials. These bores are open towards the outer side of the tray so that the finger can move from below through this bore in order to lift a vial. In that way, a mechanically simple solution for lifting a vial out of the tray without blocking the tray is provided. In an embodiment of the invention, the tray is circular and the openings through which the lifting finger can move point radially outward.

In an embodiment of the invention for use in connection with a capillary electrophoresis device, each lifting device has a head portion with a punching needle which punches a hole in a septum sealed vial when lifted from the tray. The punching needle is hollow such an end of the separation capillary can be threaded through it. When the vial has been moved by the lifting element against the head portion so that the punching needle has pierced a hole in the septum, the head portion including the vial held in the head portion are moved further upwards until the end of the separation capillary is caught by a hole in the head portion and thereafter guided through this hole and the interior of the punching needle into the vial. The use of a punching needle has the advantage that the capillary need not pierce a hole into the septum. Since the capillary is a sensitive part which might break, prior art devices often use a special pre-punched septum. In contrast thereto, the present embodiment of the invention does not require such a special septum. It is preferred that the electrode for applying the high voltage for the electrophoretic separation is also introduced into the vial through the hollow punching needle. In this case, the electrode is a tube of conductive material surrounding the capillary. The outer diameter of the electrode tube is such that it can pass through the bore in the punching needle.

The invention cannot only be used in connection with a capillary electrophoresis device, but is also suited for a liquid chromatograph for lifting a sample vial to an injection needle of the liquid chromatograph. Like in the case of an electrophoresis device, the advantage results that the sample tray is not blocked when a sample vial has been removed from the tray so that several sample preparation steps can be performed in parallel with the sample injection. The system is easily expandable by adding further lifting devices so that the desired sample preparation steps can be performed.

BRIEF DESCRIPTION OF THE DRAWINGS

Subsequently, an embodiment of the invention is explained in detail with reference to the drawings.

FIG. 3b is a magnified view of a detail in FIG. 3a.

DETAILED DESCRIPTION OF THE INVENTION

Figure 1:
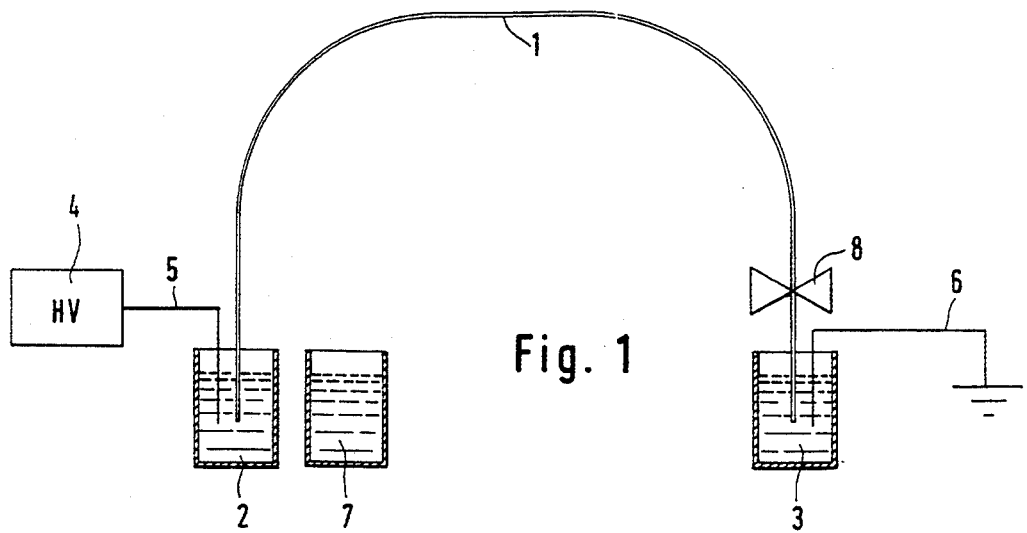
FIG. 1 is a schematic diagram illustrating the basic components of a capillary electrophoresis device.

FIG. 1 schematically depicts the components of a capillary electrophoresis apparatus. The separation capillary 1 is immersed with its input end in a first vial 2 containing electrolyte and with its output end in a second vial 3 which also contains electrolyte. An electric field is applied along the capillary 1 by a high-voltage power supply 4 via an electrode 5 at the input end of the capillary 1. An electrode 6 at the output end of the capillary 1 is connected to ground potential. A sample vial 7 contains the sample substances to be separated electrophoretically. For introducing the sample substances into the capillary 1, the vial 2 is replaced by the sample vial 7 and a plug of sample liquid is injected into the capillary 1 by suitable injection means (not shown). For example, sample liquid can be introduced by applying an overpressure on the liquid in the sample vial 7. The sample substances separated in the capillary 1 are detected by a detector 8 which is arranged at the output end of the capillary 1. The detector 8 can be, for example, a UV absorbance detector. The detector 8 is connected to a processing circuit (not shown) which produces signals indicative of the substances passing the detector. The capillary 1 is typically made of fused silica.

Figure 2:
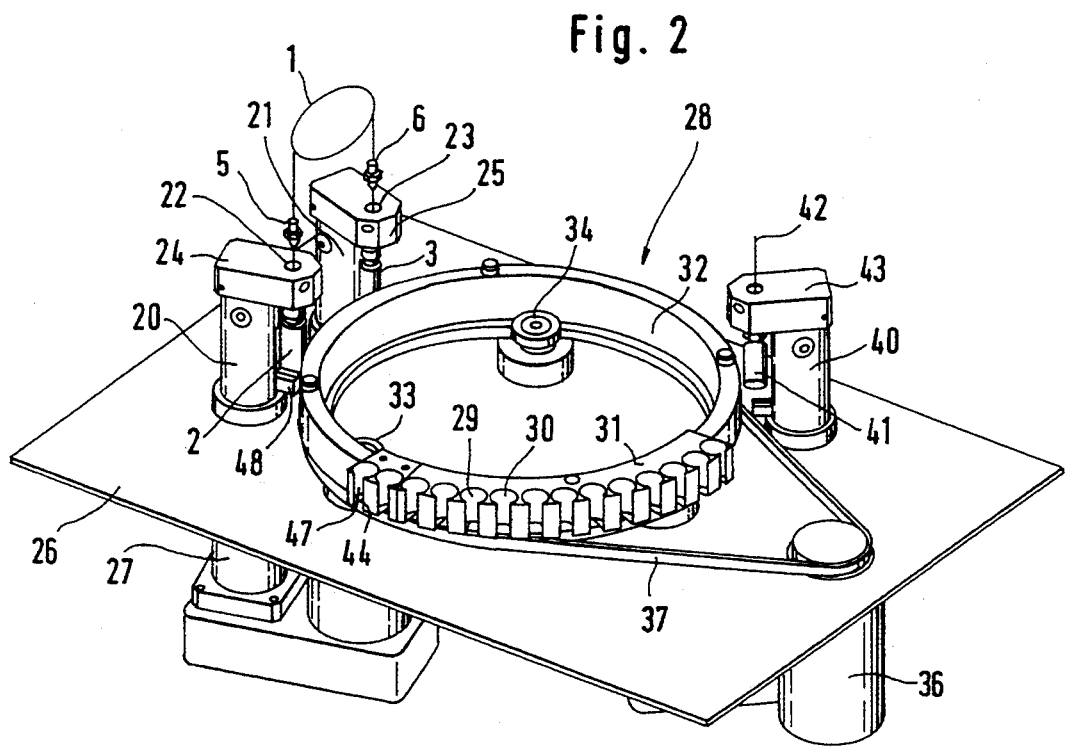
FIG. 2 shows an embodiment of a liquid handling apparatus according to the invention in a perspective view.

FIG. 2 is a perspective view of a liquid handling apparatus according to an embodiment of the invention. The separation capillary 1 is designated with reference numeral 1. The capillary 1 is wound in the shape of a coil so that a long piece of capillary tubing, for example several meters, can be arranged in a space saving manner. An electrode 5 is arranged at the input end of the capillary 1 and an electrode 6 is arranged at the output end of the capillary 1. The electrodes 5 and 6 are connected to a source of high voltage and to ground potential, respectively, by suitable electrical connections (not shown). A first vial 2 is held by a first lifting device 20 and a second vial 3 is held by a second lifting device 21. The vials 2 and 3 may both contain electrolyte or one of the vials may contain electrolyte and the other sample liquid. The two lifting devices 20 and 21 which are of identical construction are mounted to a mounting plate 26. The lifting device 20 is coupled to a motor 27 arranged below the mounting plate 26 by means of which the vial 2 can be moved in a vertical direction. The lifting device 21 is also coupled to a motor (not shown) by which the vial 3 can be vertically displaced. Details of the lifting device 20 are explained below in connection with FIG. 4.

Each of the electrodes 5 and 6 comprises an electrically conductive tube at its lower end. Each of these electrically conductive tubes surrounds an end of the capillary 1. The conductive tube of each electrode, together with the end of the capillary 1 which is guided within the conductive tube, projects through holes 22,23 in the head portions 24, 25 of the lifting devices 21 and 22 and dips into the liquids contained in the vials 2 and 3. Thus, an electric field can be applied along the capillary 1.

A ring-shaped tray 28 for receiving vials is arranged on the mounting plate 26. The tray 28 comprises a support ring 32 to which a vial holder ring 31 is mounted. The vial holder ring 31 comprises a plurality of recesses, such as recesses 29, 30 for receiving vials. for example electrolyte and sample vials. The tray segment 31 with its recesses is made of a single piece, for example of a block of aluminum machined by milling or of cast metal. This single piece 31 can be removed by an operator from the support ring 32 with all the vials inserted in the recesses and can be replaced by another tray segment wherein the desired sample and electrolyte vials are arranged. This provides for an easy and convenient handling of the sample and electrolyte vials.

Figure 3A:
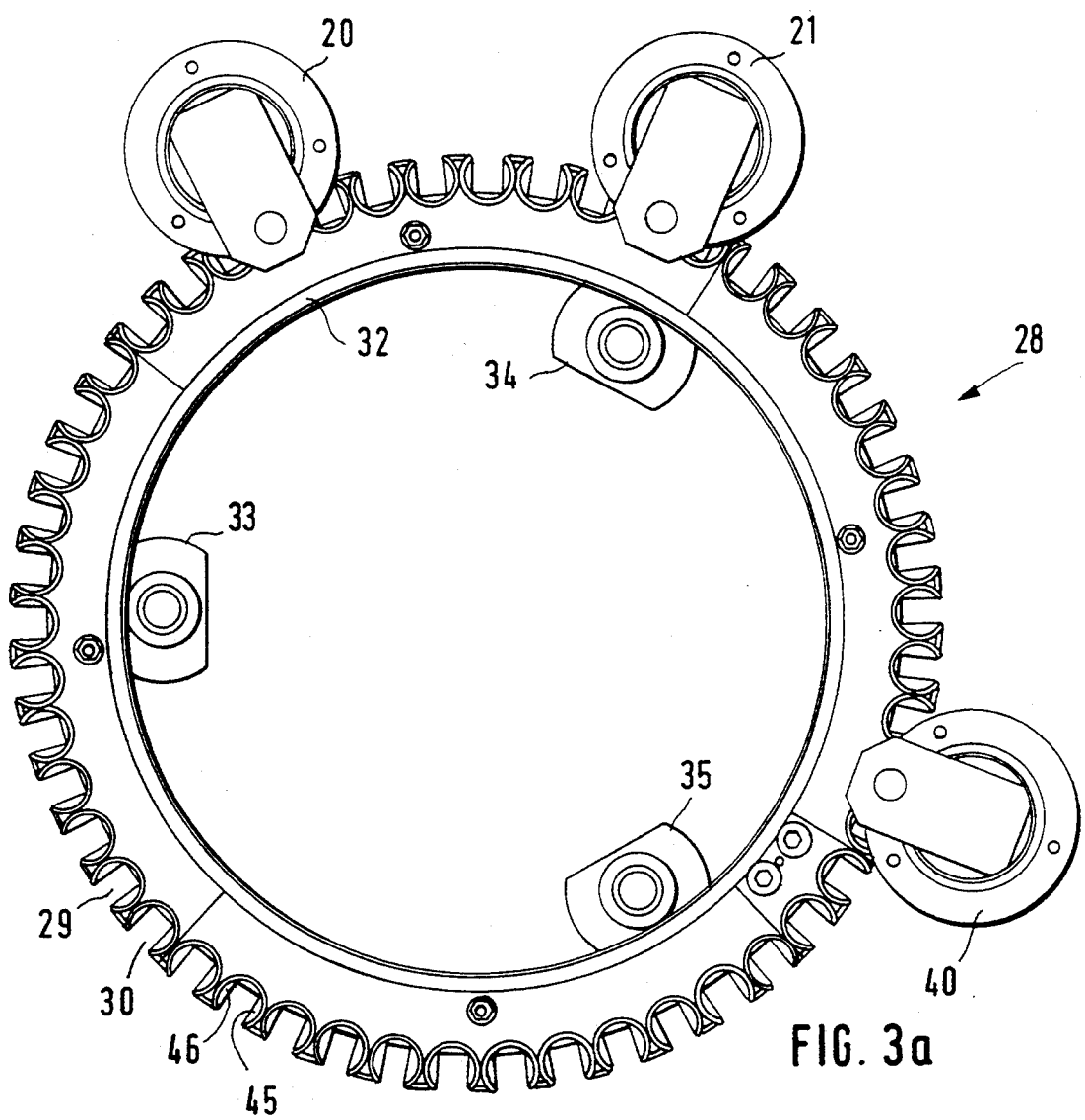
FIG. 3a is a top view on an apparatus according to the invention.

In the embodiment shown, the vial holder ring 31 is only a segment corresponding to a quarter of a circle. It is understood, however, that vial holders may be arranged along the entire circumference of the support ring 32. It is possible, for example, to arrange additional tray segments having the same shape as segment 31 on the support ring 32 or to use instead of the quarter circle segment a different circle segment or even a full circle. In FIG. 3a is shown an embodiment wherein vial holders are provided along the entire circumference of a circle. The tray in this embodiment may be made of a single piece or it may consist of four segments of the type like the segment 31 in FIG. 2.

Referring again to FIG. 2, the ring 32 is supported by bearings 33, 34 and 35 which are arranged within the ring 32 such that the ring can be turned around an axis through the center of the ring. For turning the ring 32, a motor 36 and a toothed belt 37 running around the outer surface of the support ring 32 and the drive shaft of the motor 36 are provided. Thus, the tray 28 can be turned so that a desired vial can be positioned at the lifting devices 20 or 21. The lifting devices have a lifting mechanism by which the vial can be lifted from the tray 28 to the head portions 24 or 25 of the lifting devices. This lifting mechanism will be explained in more detail with reference to FIG. 4. Vials which have been positioned in the lifting devices 20 or 21, for example vials 2 or 3, can be lowered again into a free recess of the tray 28, such as recess 29 or recess 30. When the vials have been positioned in the tray, the tray may be turned to a new position so that a different vial can be withdrawn from the tray. As is shown in FIG. 2, the vials 2 and 3 are lifted by the first lifting device 20 and by the second lifting device 21 against the head portions 24 and 25, so that the ends of the capillary 1 and the associated electrodes dip into the liquids contained in the vials 2 and 3, respectively.

A third lifting device 40 identical in construction to the lifting devices 20 and 21 is arranged at the tray 28. The function of this third lifting device is to replenish electrolyte in the electrolyte vials, such as vial 41. For this purpose, a replenishment needle 42 is provided which projects through the head portion 43 of the lifting device 40. The replenishment needle 42 is connected with its one end to a pump (not shown) by means of which liquid can be sucked from the vial 41 when the needle dips into it. When used electrolyte in a vial is to be replenished, the tray is rotated by means of the motor 36 until the corresponding vial is positioned at the lifting device 40, then the lifting mechanism lifts the vial from the tray up against the head portion of the lifting device 40 so that the replenishment needle 42 is immersed in the electrolyte. This corresponds to the situation illustrated in FIG. 2. Then, the pump connected to the replenishment needle 42 is activated so that the electrolyte is sucked out of the vial 41. The used electrolyte is then pumped into a waste container (not shown).

Thereafter, fresh electrolyte is introduced into the vial 41 from an electrolyte supply container (not shown), and the vial is lowered again into a recess of the tray 28. The vial with the replenished electrolyte can then be transported by a corresponding rotation of the tray 28 to one of the lifting devices 20 or 21 where it can be brought again into contact with an end of the separation capillary 1 for performing an electrophoretic separation.

In cases where it is necessary to cool or heat the sample vials, a cooling or heating apparatus can be arranged at the inner edge of the support ring 32. For example, cooling coils can be fixed to the circular inner edge of the ring 32. Since the ring is typically made of metal, good thermal conductivity is ensured.

In FIG. 3a is shown a top view on an apparatus according to the invention. The apparatus substantially corresponds to the apparatus shown in FIG. 2 except that the recesses for receiving sample and electrolyte vials are provided along the entire circumference of the tray 28. The apparatus according to FIG. 2 comprises recesses only along a quarter circle, but it could be converted to the apparatus shown in FIG. 3 by providing four segments like segment 31 so that a full circle results. The first lifting device 20 and the second lifting device 21 are arranged near the tray 28 and comprise means for lifting vials from the tray 28 upwards to bring them into contact with the ends of the capillary 1 for performing an electrophoretic separation. The third lifting device 40 which has the same design as the other two lifting devices serves for replenishing electrolyte as explained above in connection with FIG. 2.

The support ring 32 is guided by the bearings 33, 34 and 35. The support ring can thus rotate around an axis which extends perpendicular to the plane of the paper through the center of the ring 32. The support ring is driven via the toothed belt 37 as shown in FIG. 2.

Figure 3B:
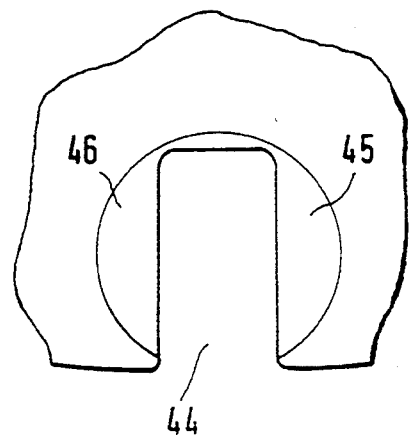

The recesses, such as recesses 29 and 30, have substantially the shape of a cylinder so that a cylindrical vial fits into them, respectively. In order to explain the shape of the recesses in more detail, reference is now made to FIG. 3b which is an enlarged view of one of the several identical recesses at the periphery of the tray 28. Like FIG. 3a, FIG. 3b is a top view. The bottom of the cylindrical recess wherein a vial can be positioned comprises a slot 44 through which a finger 48 of the lifting device can be introduced from below. To the left and to the right of this slot, support faces 45 and 46 are provided which support the bottom of the vial in the recess. The slot 44 extends upwards, i.e. parallel to the longitudinal axis of the cylindrical recess (perpendicular to the plane of the paper). This lateral slot can be better seen in FIG. 2 where it is designated with reference numeral 47. The provision of the slot 44 extending into slot 47 enables the removal of a vial from the tray by one of the lifting devices. For this purpose, each lifting device comprises a finger, such as finger 48, which can be positioned below a vial supported by faces 45 and 46 and moved upwards through the slot 44 and the slot 47. When the finger 48 moves upwards, it pushes the vial upwards. Details of this lifting mechanism will be described in the following in connection with FIG. 4.

Figure 4:
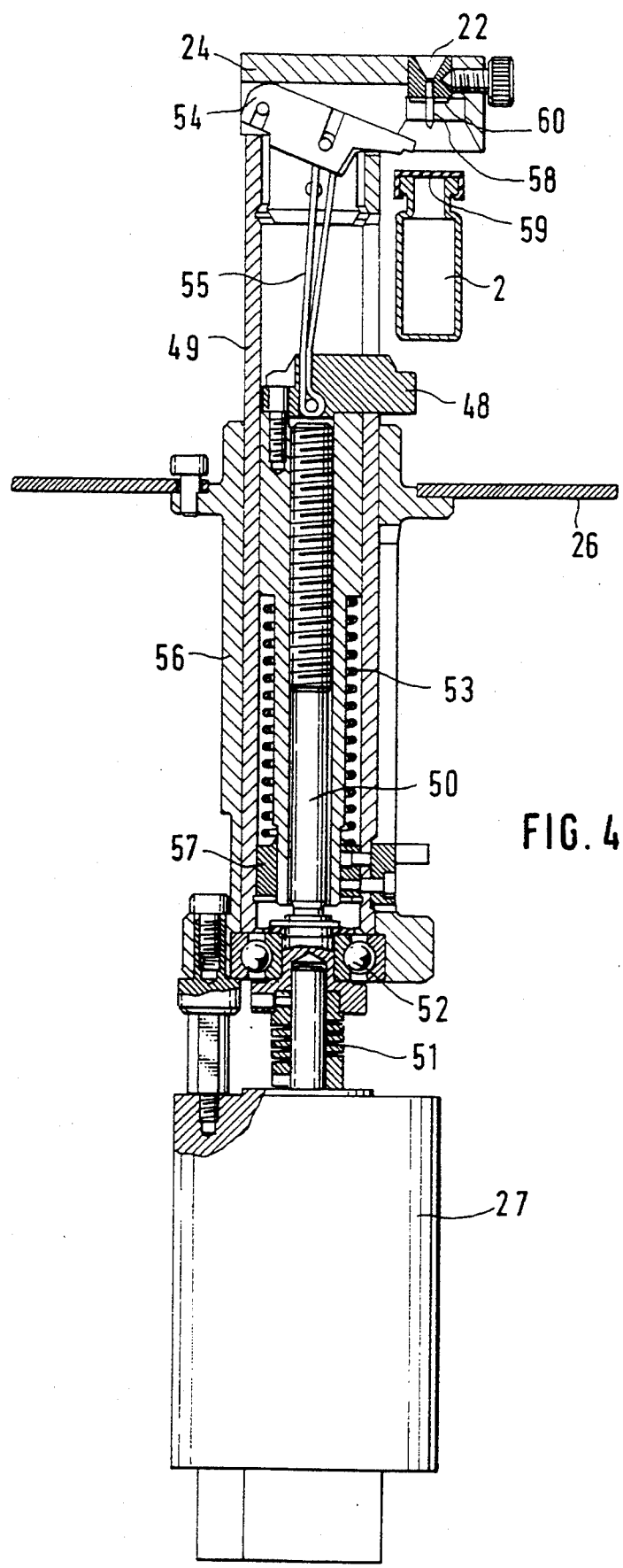
FIG. 4 is a detailed cross sectional view of a lifting mechanism shown in FIG. 2.

FIG. 4 is a cross section through the lifting device 20 shown in FIG. 2. The other lifting devices 21 and 40 have the same design and will therefore not be described separately. The lifting device 20 comprises a cylindrical housing 56 which is fastened to the mounting plate 26. Arranged inside the housing 56 is a guide sleeve 49 to which the head portion 24 is fastened. The guide sleeve 49 can move inside the housing 56 along the axis of the cylinder. The lower portion of the guide sleeve 49 comprises a metal ring 57. A spring 53 acts on the metal ring 57 and urges the guide sleeve 49 against a stop 52. The stop 52 is a ball bearing which also serves as a bearing for a spindle drive 50.

A lifting finger 48 is provided for lifting a vial 2 out of the tray 28. The lifting finger 48 is moved via the spindle drive 50 by a motor 27. The motor 27 and the spindle drive 50 are connected via a coupling 51. By a rotation of the spindle drive 50, the finger 48 is moved upwards and carries along the vial 2. The end of the finger 48 which is in contact with the vial 2 can be provided with a step as shown in FIG. 4 in order to secure the vial against displacement. When the finger 48 together with the vial 2 moves upwards, the vial 2 is finally pressed against the head portion of the lifting device so that a punching needle 58 produces a hole in the septum 59 of the vial 2. The punching needle 58 is a hollow needle, The inner diameter of the punching needle 58 is selected such that the capillary 1 and the electrode tube surrounding the capillary 1 can pass through it. Further details of this arrangement will be explained below.

When the spindle 50 is further rotated so that the force urging the vial 2 against the head portion 24 of the lifting device is greater than the prestressing force of the spring 53, the lifting finger 48 moves the vial 2 together with the head portion 24 upwards towards the ends of the capillary which is held in place by suitable means (not shown). The upward movement is continued until an end of the capillary 1 projects through the opening 22 and the punching needle 58 into the vial 2. On the top side of the punching needle is a funnel 22 which has the function to capture the capillary 1 when the head portion is moved upwards and to provide for sealing at a corresponding counter-cone associated with the capillary and the surrounding electrode tube. When the vials at both ends of the capillary 1 have been brought into registration, sample can be injected into the capillary and the electrophoretic separation can be performed.

The injection is preferably performed by applying a pressure difference between the vial at the input end and the vial at the output end of the capillary 1. For this purpose, an overpressure is applied to the liquid in the vial 2 through a tube communicating with the bore in the punching needle 58. The tube for applying overpressure is arranged perpendicularly to the plane of the paper in FIG. 4. Escaping of the applied pressure is prevented firstly by a sealing arrangement (not shown) associated with the capillary and the surrounding tube-shaped electrode to be introduced in the funnel 22, and secondly by an annular cutting edge 60. The cutting edge 60 cuts into the septum 59 when the vial is firmly pressed against the head portion 24 and thus provides for sealing. Further details of the sealing of the capillary and electrode arrangement are subject of a European patent application entitled "Apparatus for Performing Capillary Electrophoresis", filed by applicant of the present European patent application on the same date as the present application (applicant's internal docket number: 20-92-01 4).

When the vial 2 is again to be positioned in the tray 28, the motor 27 turns the spindle 50 in the reverse direction so that the finger 48 moves downwards. The finger 48 moves through the lateral slot 47 and the slot 44. The head portion 24 together with the vial 2 will follow this downward movement until the guide sleeve 49 strikes on the stop 52. In order to go further downwards, the spring 53 has to be compressed. During the downward movement, the vial 2 will stick to the punching needle 58. In order to ensure that the vial 2 is removed again from the punching needle 58 and placed in a corresponding recess of the tray 28, a rocking lever 54 and an actuation belt 55 connecting the lever 54 with the finger 48 are provided. When the finger 48 has been moved sufficiently far downwards through the slots 47 and 44, the actuation belt 55 is tightened causing a tilting of the rocking lever 54 whereby the vial 2 is stripped off the punching needle 58.

After the vial 2 has been put again into the tray 28, a different vial, for example a vial with a different sample than the previous one, can be brought into contact with an end of the capillary 1. For this purpose, the tray 28 is turned until the desired sample vial is at the position of the lifting device 20, then the finger 48 is lifted so that it moves through the slot in the bottom of the recess wherein the vial is positioned and the lateral slot in the wall. When lifting the vial from its position in the tray 28, it is guided in the cylindrical bore until it is caught by the head portion of the lifting device. In that way, it is ensured that the vial is safely lifted to its final position.

In the same way, the vial 3 can be replaced by a different vial. If, for example, the vial 3 is an electrolyte vial, and the electrolyte is to be replenished after an electrophoretic separation, the vial is lowered into the tray 28 by the lifting device 21, the tray is turned until a vial with fresh electrolyte is at the position of the lifting device 21, then the vial is lifted by the lifting device 21 until the second end of the capillary 1 dips into the electrolyte.

The vial 3 with the used electrolyte can be moved by an appropriate rotation of the tray 28 to the position of the third lifting device 40, and then lifted until the replenishment needle 42 is immersed in the liquid in the vial 3. Then, the liquid can be sucked out of the vial and new electrolyte can be filled into it. The replenishment of used electrolyte may be performed while an electrophoretic separation takes place in the capillary 1.

It is an important advantage of the present invention that the tray 28 is freely movable after a vial has been taken out of the tray 28 by one of the lifting devices 20, 21 or 40. This is due to the fact that the fingers of each lifting device, for example finger 48, are arranged above the tray 28 when the vial has been lifted to its final position. Since the tray can be rotated after lifting of a vial, it is possible that several tasks are performed in parallel. If, for example, vials 2 and 3 have been positioned at the ends of the capillary 1 and an electrophoretic separation is performed, one can at the same time replenish electrolyte in a vial used in a previous electrophoretic separation. Furthermore, it is possible with an apparatus of the invention to perform the replenishment of the electrolyte and the rinsing of the separation capillary in parallel.

In contrast thereto, the trays in prior art devices are blocked when a vial has been lifted from it. Thus, when an electrophoretic separation is performed in such a prior art device with the vials being lifted to the ends of the capillary, the trays are not movable any more. Consequently, no further vial handling actions are possible.

In a further development of the apparatus shown in FIG. 2, additional lifting means of the type of lifting means 20 are provided near the tray 28. These lifting means are used to remove vials from the tray to perform sample pretreatment, for example by heating or mixing. Furthermore, a bar code reader could be provided at one of these additional lifting stations to identify vials which have been provided with a bar code label. Also when using such additional lifting means, the advantage of the invention applies that the tray is freely movable when a vial has been lifted. In that way, sample pretreatment, replenishing, identification of vials by a bar code reader can all be performed in parallel.

According to a practical example of the invention, the tray 28 has a diameter of 24 cm and can accommodate 50 vials. The recesses for the vials have a diameter of 1,2 cm and a depth of 1,8 cm. A typical vial to be inserted in such a recess has a diameter of 1,15 cm and a height of 3,3 cm. The head portions and the guide sleeves of each lifting device are made of a plastic material which is high-voltage proof. An alternative material could be ceramics.

The above described embodiment of the invention comprises a circular tray for accommodating the various vials, and the circular tray is rotated to transport the vial to the desired lifting means. It is understood, however, that alternative embodiments of the tray are possible. The tray could be, for example, rectilinear so that the vials are arranged along a straight line instead of a circle as with the embodiment shown in FIG. 2. In such an alternative embodiment, the tray has the shape of a bar having a plurality of recesses for accommodating the vials and slots at the bottom and at a side through which the finger of the lifting device passes to lift the vial out of the tray. The lifting devices are located along a straight line and the tray is moved linearly along this line or parallel thereto.

The invention cannot only be used in connection with an electrophoresis system, but also with other analytical devices such as a liquid chromatograph. In a liquid chromatograph, the apparatus of the invention can be used for accommodating and manipulating various sample vials including injection of the sample into the chromatographic system. The lifting devices of the apparatus of the invention are used to lift the sample vial to a stationary injection needle (similar to the replenishment needle shown in FIG. 2) by which the sample is sucked into the chromatograph under the action of a pump. Like in the electrophoresis system, additional lifting means can be provided near the tray which enable a sample pretreatment. Examples for such sample pretreatment are heating, mixing, dispensing. In the case of dispensing, liquids from supply containers can be mixed in the vial by means of switching valves which are connected to a needle. The advantages relative to conventional liquid chromatographic injection systems are, similar as in the case of an electrophoresis system, that the tray is not blocked when a vial has been removed so that injection and sample pretreatment steps can be performed in parallel. A further advantage is that the system can easily be expanded just by adding further lifting devices. As in the electrophoresis device, various embodiments of the tray are possible, for example a circular or a linear tray.

We claim:

1. Apparatus for handling liquid vials in an analytical device, the apparatus comprising:
a capillary tube having first and second ends; potential means for operating said apparatus to perform an electrophoretic separation;
a single movable tray for receiving liquid-containing vials, said tray comprising a plurality of vial holders for holding vials, a first lifting device arranged in proximity of the tray for lifting a first selected vial out of a vial holder and into engagement with said first end of said capillary tube, said first lifting device arranged to enable the tray to remain movable to bring a second vial into proximity of said second end of said capillary tube when the first vial has been lifted sufficiently far out of the vial holder to engage said first end of said capillary tube and a second lifting device for lifting said second vial into communication with said second end of said capillary tube so as to perform an electrophoretic separation of a sample under control of said potential means, and
drive means for moving the tray to position selected vials in juxtaposition to said first and second lifting devices.

2. An apparatus as in claim 1, wherein the first lifting device comprises a movable lifting element positioned underneath a bottom surface of said first selected vial and which is movable to lift said first selected vial out of the vial holder.

3. An apparatus as in claim 2, wherein the vial holder comprises a recess formed in a block of material, said recess shaped to substantially encompass an outer shape of the vial, and wherein an opening is provided in said block of material through which the lifting element is moved to lift the vial out of the holder.

4. An apparatus as in claim 1 wherein the tray is circular and is rotated around a center axis to position a selected vial at said at least one lifting device.

5. An apparatus as in claim 1, wherein the tray is elongated and is moved linearly to position a selectable vial at a lifting device.

6. An apparatus for handling liquid vials, said apparatus comprising:
a tube with a first end and a second end;
a single tray for receiving liquid-containing vials, said tray comprising a plurality of vial holders for holding the vials,
at least first and second lifting devices arranged in proximity of the tray, said first lifting device for lifting a first vial out of a vial holder and into engagement with said first end of said tube, said first lifting device arranged to enable said single tray to remain movable when said first vial is moved out of said vial holder and into engagement with said first end, and said second lifting device for lifting a second vial out of a vial holder and into engagement with said second end of said tube, whereby fluid communication is enabled between said first vial and said second vial, and
drive means for moving the tray to position selected vials in juxtaposition to said first and second lifting devices.

7. An apparatus as in claim 6, wherein each lifting device comprises:
a lifting element which is vertically displaceable and which can be positioned underneath a bottom surface of the vial,
a head portion for receiving an upper part of a vial when the vial has been lifted by the lifting element, and
a punching needle arranged in the head portion for punching a hole in a septum of the vial when the vial is lifted towards the head portion by the lifting element.

8. An apparatus as in claim 7, wherein the head portion is vertically displaceable and wherein the head portion is moved upwards towards an end of a tube after the upper part of the vial has been received in the head portion.

9. An apparatus as in claim 8, wherein the punching needle is a hollow-needle having an inner diameter sufficient for guiding an end of the tube through it, the apparatus further comprising:
a funnel at the end of the punching needle opposite to an end of the tube, such that an end of the tube is captured by the head portion.

10. An apparatus as in claim 1, further comprising: a rocking lever in the head portion of the lifting device and an actuation belt fastened to the rocking lever and to the lifting element, whereby the actuation belt is tightened when the lifting element has moved downwards a predetermined distance such that the rocking lever is tilted, whereby the vial is stripped off the punching needle.

11. An apparatus as in claim 6, further, comprising: a third lifting device and a replenishment needle which can be introduced into an electrolyte vial which has been lifted out of the tray by the third lifting device.

12. An apparatus as in claim 7, further comprising a third lifting device and a replenishment needle which can be introduced into an electrolyte vial which has been lifted out of the tray by the third lifting device.

* * * * *